United States Patent
O'Shea et al.

(10) Patent No.: US 9,885,090 B2
(45) Date of Patent: Feb. 6, 2018

(54) ADENOVIRAL TUMOR DIAGNOSTICS

(71) Applicant: Salk Institute for Biological Studies, La Jolla, CA (US)

(72) Inventors: Clodagh O'Shea, San Diego, CA (US); Colin Powers, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 14/485,488

(22) Filed: Sep. 12, 2014

(65) Prior Publication Data

US 2015/0005397 A1 Jan. 1, 2015

Related U.S. Application Data

(63) Continuation of application No. PCT/US2013/031646, filed on Mar. 14, 2013.

(60) Provisional application No. 61/610,970, filed on Mar. 14, 2012.

(51) Int. Cl.

| C07K 16/28 | (2006.01) |
| C07K 14/705 | (2006.01) |
| C07K 16/30 | (2006.01) |
| A61K 39/395 | (2006.01) |
| C07K 14/725 | (2006.01) |
| C12Q 1/68 | (2006.01) |
| C12N 15/86 | (2006.01) |
| C12N 7/00 | (2006.01) |
| G01N 33/574 | (2006.01) |

(52) U.S. Cl.
CPC .......... *C12Q 1/6897* (2013.01); *C12N 7/00* (2013.01); *C12N 15/86* (2013.01); *G01N 33/57415* (2013.01); *G01N 33/57492* (2013.01); *C12N 2710/10045* (2013.01); *C12N 2710/10331* (2013.01); *C12N 2710/10343* (2013.01); *C12N 2830/008* (2013.01); *C12N 2830/85* (2013.01); *G01N 2800/7028* (2013.01)

(58) Field of Classification Search
CPC .......... C12N 15/86; C12N 2830/008; C12N 2830/85; C12N 2710/10045; C12N 2710/10331
See application file for complete search history.

(56) References Cited

U.S. PATENT DOCUMENTS

| 7,943,373 | B2 | 5/2011 | Fujiwara et al. |
| 2004/0219543 | A1 | 11/2004 | Wirtz |
| 2008/0112929 | A1* | 5/2008 | Kovesdi ........... C12N 15/86 424/93.2 |
| 2008/0242608 | A1* | 10/2008 | Bonni ............... A61K 38/45 514/1.1 |
| 2009/0202565 | A1 | 8/2009 | Labow et al. |
| 2010/0047208 | A1* | 2/2010 | Ke ..................... A61K 48/005 424/93.2 |
| 2010/0075951 | A1 | 3/2010 | Cardin et al. |
| 2010/0075998 | A1 | 3/2010 | Vanotti et al. |
| 2010/0151576 | A1 | 6/2010 | Li et al. |
| 2010/0292166 | A1 | 11/2010 | Lee et al. |
| 2011/0256524 | A1 | 10/2011 | Lee et al. |

FOREIGN PATENT DOCUMENTS

| CN | 1330715 A | | 1/2002 |
| CN | 1380420 A | | 11/2002 |
| CN | 102191245 | * | 9/2011 |
| CN | 102191245 A | | 9/2011 |
| EP | 1593742 | * | 11/2005 |
| JP | 2005-525779 | | 9/2005 |
| JP | 2008-517627 | | 5/2008 |
| JP | 2010-527324 | | 8/2010 |
| JP | 2011-524904 | | 9/2011 |
| WO | WO 00/22137 | | 4/2000 |
| WO | WO2008150496 | * | 12/2008 |
| WO | WO2010024483 | * | 3/2010 |
| WO | WO 2012/003287 | | 1/2012 |
| WO | WO 2012/024351 | | 2/2012 |

OTHER PUBLICATIONS

Warram et al., "A Genetic Strategy for Combined Screening and Localized Imaging of Breast Cancer," *Mol Imaging Biol* 13:452-461, 2011.
Extended European Search Report for European Application No. 13760821.2, dated Sep. 30, 2015.
English-language abstract of CN102191245A.
English-language abstract of CN1380420A.
Office Action and Search Report from China Application No. 201380014047.7, dated Aug. 5, 2015 (English translation).
Murakami et al., "Chimeric Adenoviral Vectors Incorporating a Fiber of Human Adenovirus 3 Efficiently Mediate Gene Transfer into Prostrate Cancer Cells," *The Prostate*, vol. 70:362-376, 2009.

\* cited by examiner

*Primary Examiner* — Barry A Chestnut

(74) *Attorney, Agent, or Firm* — Klarquist Sparkman, LLP

(57) ABSTRACT

Compositions and methods for detecting a cancer in a subject using a recombinant reporter adenovirus are described. In particular, recombinant adenovirus is used to diagnose a cancer in a patient and further used for screening compounds effective in treating the cancer in said patient.

18 Claims, 10 Drawing Sheets

ADENOVIRAL TUMOR DIAGNOSTICS

CROSS-REFERENCE TO RELATED APPLICATIONS

This is a continuation of International Application No. PCT/US2013/031646, filed Mar. 14, 2013, published in English under PCT Article 21(2), which claims the benefit of U.S. Provisional Application No. 61/610,970, filed Mar. 14, 2012. The above-listed applications are hereby incorporated by reference in their entirety.

STATEMENT OF GOVERNMENT SUPPORT

This invention was made with government support under grants R01HG004876, R21RR024453, and R43RR031424 awarded by the National Institutes of Health. The Government has certain rights in the invention.

BACKGROUND

The spread of cells from a solid tumor to remote sites in the body, a process known as metastasis, is responsible for over 90% of all cancer-related deaths. Cells originating from the primary tumor can enter the circulatory system and extravagate to invade, colonize, and proliferate in organs and tissues far from the primary neoplasm. Thus, the detection of these circulating tumor cells (CTCs) provides an invaluable opportunity for both the early identification and therapeutic targeting of metastatic cancer cells (Cristofanilli, 2004; de Bono, 2008). Current techniques for detection of CTCs include reverse transcriptase-polymerase chain reaction (RT-PCR), flow cytometry, fluorescence in situ hybridization, and, more recently, microfluidics. Unfortunately, RT-PCR does not distinguish between viable metastatic CTC versus nucleic acids or cellular fragments originating from the primary tumor.

Antibody-based techniques cannot be used for detection of all cancers, but only those cancers that express the most common and well-characterized markers. CTC enumeration of current systems only provides one layer of information regarding cancer diagnosis. One device, CellSearch® (Veridex, Raridan N.J.), has demonstrated commercial success for CTC analysis and is FDA approved for breast, prostate, and colon, while ovarian, rectum, and lung await approval. Limitations of the CellSearch® system include: (a) dependence on the level of EpCAM expression (Punnoose E A, et al., *PLoS ONE*. 2010; 5(9):e12517), (b) no use of mesenchymal markers (Punnoose E A, et al., *PLoS ONE*. 2010; 5(9):e12517), (c) reliance on antibody affinity for capture (Nagrath S, et al., *Nature*, 2007; 450(7173):1235-9.18097410), and most importantly (d) the absence of CTC phenotypic characterization.

There is no antibody that is 100% tumor or tissue specific and antibodies bind to viable as well as dead CTCs. Thus there is a need for a more sensitive, specific, and widely applicable technology for detection of rare CTC in blood. Further, there is a desperate need to develop new diagnostic agents and tools that not only detect and capture CTCs but also quantify their malignant potential and identify 'up-front' the therapies that are most effective in ablating an individual patient's tumor.

Despite the complexity and variability of cancers at a genome scale, a unifying theme is their growth deregulation phenotypes, the so-called hallmarks of cancer, which are conferred by mutations in a relatively small number of key pathways. Rather than focus on detecting individual genetic lesions that are numerous and highly variable between tumors, Applicants created diagnostic viruses that incorporate multiple transcriptional and molecular modules in their genomes to infect and detect a patient's tumor, report its molecular 'hallmarks' and its response to different therapies 'up-front'. Using these agents, the molecular lesions and malignant characteristics of any given tumor can be rapidly discerned (within 24 hours) and scored via a standardized automated-platform. Furthermore, these agents could also be used as reporters to determine rapidly and directly if a patient's tumor is likely to respond to a particular therapy.

SUMMARY

In one aspect, a method of detecting a cancer in a subject is provided. The method includes administering a recombinant reporter adenovirus to a subject. The recombinant reporter adenovirus is allowed to infect a cancer cell within the subject thereby forming a reporter infected cancer cell. A sample including the reporter infected cancer cell is obtained from the subject and the reporter infected cancer cell is detected thereby detecting a cancer in the subject.

In another aspect, a method of detecting a cancer in a subject is provided. The method includes obtaining from a subject a sample including a cancer cell. A recombinant reporter adenovirus is contacted with the cancer cell. The recombinant reporter adenovirus is allowed to infect the cancer cell thereby forming a reporter infected cancer cell and the reporter infected cancer cell is detected thereby detecting a cancer in said subject.

In another aspect, a method of determining whether a test compound inhibits growth of a cancer cell from a cancer patient is provided. The method includes obtaining from a subject a sample including a cancer cell. A recombinant reporter adenovirus is contacted with the cancer cell. The recombinant reporter adenovirus is allowed to infect the cancer cell thereby forming a reporter infected cancer cell. The reporter infected cancer cell is allowed sufficient time to grow. A level of growth of the reporter infected cancer cell is determined and the level is compared to a control level, wherein a low level compared to the control level indicates the test compound inhibits growth of the cancer cell from the patient.

In another aspect, a method of isolating a reporter infected cancer cell within a sample from a subject is provided. The method includes separating the reporter infected cancer cell from a non-infected cell, wherein the separating is at least partially based on an expressed reporter gene phenotype of the reporter infected cancer cell.

In another aspect, a recombinant reporter adenovirus including a cancer cell reporter module and a cancer cell binding module is provided.

In another aspect, a method of detecting a cancer in a subject is provided. The method includes administering a recombinant reporter adenovirus provided herein including embodiments thereof to a subject. The recombinant reporter adenovirus is allowed to infect a cancer cell within the subject thereby forming a reporter infected cancer cell. A sample is obtained from the subject including the reporter infected cancer cell and the reporter infected cancer cell is detected thereby detecting a cancer in the subject.

In another aspect, a method of detecting a cancer in a subject is provided. The method includes obtaining from a subject a sample including a cancer cell. A recombinant reporter adenovirus provided herein including embodiments thereof is contacted with the cancer cell. The recombinant reporter adenovirus is allowed to infect the cancer cell thereby forming a reporter infected cancer cell and the reporter infected cancer cell is detected thereby detecting a cancer in the subject.

In another aspect, a method of determining whether a test compound inhibits growth of a cancer cell from a cancer patient is provided. The method includes obtaining from a subject a sample including a cancer cell and contacting a recombinant reporter adenovirus provided herein including embodiments thereof with the cancer cell. The recombinant reporter adenovirus is allowed to infect the cancer cell thereby forming a reporter infected cancer cell. The reporter infected cancer cell is allowed sufficient time to grow and a level of growth of the reporter infected cancer cell is determined. The level is compared to a control level, wherein a low level compared to the control level indicates the test compound inhibits growth of the cancer cell from the patient.

In another aspect, a kit for detecting cancer is provided. The kit includes a recombinant reporter adenovirus provided herein including embodiments thereof.

In another aspect, a kit for screening a cancer drug is provided. The kit includes a cancer inhibiting compound and a recombinant reporter adenovirus provided herein including embodiments thereof.

In another aspect, a kit for isolating a cancer cell is provided. The kit includes a device for detecting an expressed reporter gene phenotype and a recombinant reporter adenovirus provided herein including embodiments thereof.

BRIEF DESCRIPTION OF THE DRAWINGS

FIG. 2 upper panel: Genome divided into transcriptional and functional modules and cloned into plasmids. FIG. 2 middle panel: The E1, E3, and E4 modules are modified with tumor specific promoters driving fluorescent proteins in order to highlight CTCs. FIG. 2 lower panel: Systematic multi-site specific in vitro re-assembly and reconstitution of virus.

DETAILED DESCRIPTION

I. Terms

Figure 1:
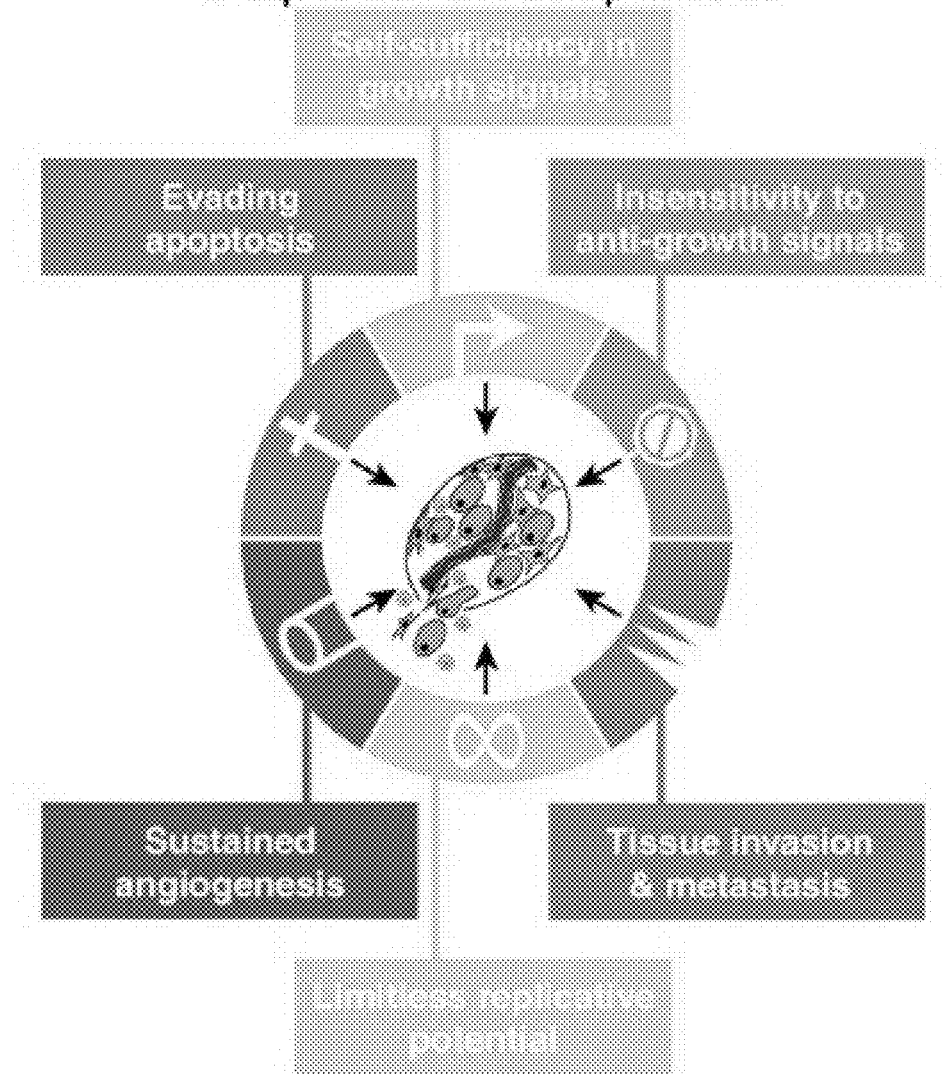
FIG. 1. Hallmarks of cancer.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Construction of suitable vectors containing the desired therapeutic gene coding and control sequences may employ standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides may be cleaved, tailored, and re-ligated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0)

and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, virus, nucleic acid, protein, or vector, indicates that the cell, virus, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecule can be a sequence encoding complete proteins or functional portions thereof. Typically, a nucleic acid vector, including the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a adenoviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

Expression of a transfected gene can occur transiently or stably in a host cell. During "transient expression" the transfected nucleic acid is not integrated into the host cell genome, and is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision.

The terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division. The term does not imply that all cells in the culture survive or grow or divide, as some may naturally senesce, etc. Cells are typically cultured in media, which can be changed during the course of the culture.

The terms "media" and "culture solution" refer to the cell culture milieu. Media is typically an isotonic solution, and can be liquid, gelatinous, or semi-solid, e.g., to provide a matrix for cell adhesion or support. Media, as used herein, can include the components for nutritional, chemical, and structural support necessary for culturing a cell.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

In compositions including an "additional," "further," or "second" component (e.g. cancer cell reporter module, reporter gene phenotype), the second component as used herein is different from the other components or first component. A "third" component is different from the other, first, and second components, and further enumerated or "additional" components are similarly different.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinosa carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy,* 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

II. Methods

Figure 9:
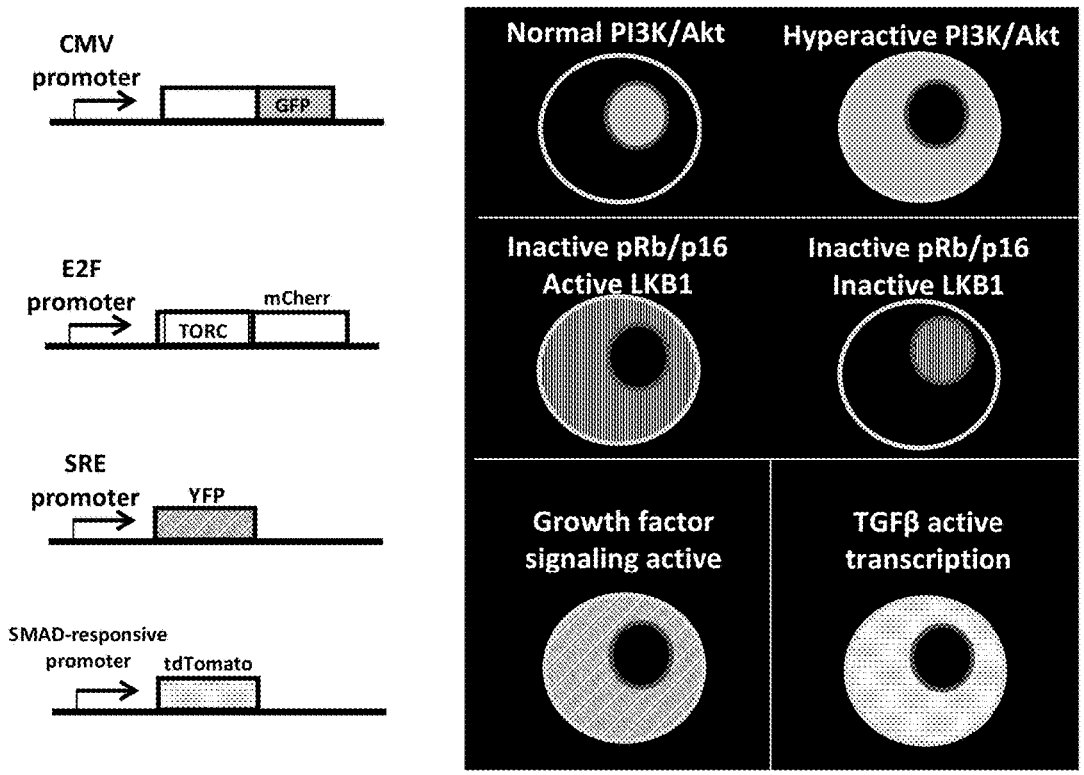
FIG. 9. Fluorescent readouts for selected tumor diagnostic pathways. This figure lists an initial panel of four diagnostic expression cassettes (left side) and their expected phenotype in cells (right side). The CMV-[Foxo3-GFP] cassette is constitutively active, and thus GFP is expressed in all cell types where the CMV promoter is active. In cells where PI3K/Akt activity is low, such as non-tumor tissue, the Foxo3-GFP fusion localizes to the nucleus. However, in cells where PI3K/Akt activity is high, such as in tumor cells, the Foxo3-GFP fusion localizes to the cytoplasm. The E2F-[mCherry-CRTC2] cassette is only active in cells that have inactive pRB, such as in almost all tumors. In these cells, the mCherry-CRTC2 fusion is cytoplasmic if the tumor suppressor Lkb1 is intact. However, in tumor cells that have lost Lkb1 function, the mCherry-CRTC2 fusion is located in the nucleus. The serum response element (SRE) promoter expresses YFP only in cells that have activated growth factor signaling or mitogen stimulation, indicative of rapidly dividing cells such as tumors. Lastly, the SMAD-responsive promoter cassette drives expression of tdTomato in cells where TGFβ signaling is active, which has been linked to a metastatic phenotype in certain cancers. When combined, these four expression cassettes provide information on five different cancer-relevant pathways.
Figure 10:
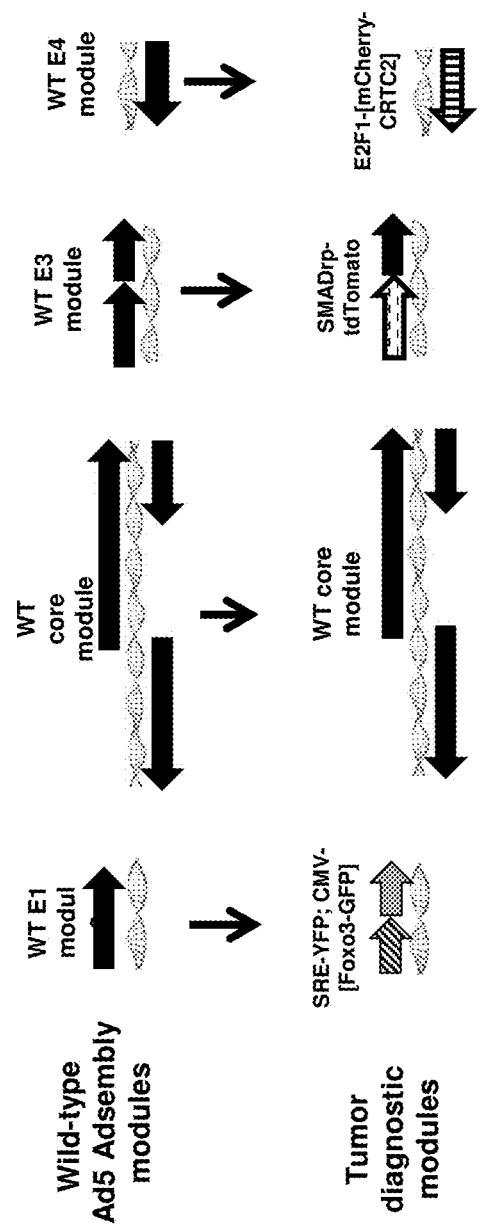
FIG. 10. Manipulation of Adenovirus Adsembly modules to create tumor diagnostic viruses. Viruses were created using the Adsembly genome assembly method. This figure diagrams in which Adsembly modules each of the initial four cancer diagnostic expression cassettes was placed. Two cassettes were cloned into the E1 module, as it has been shown to tolerate dual-expression cassettes in previous experiments. The E3A/E3B portion of the E3 module was deleted and replaced with a single cassette. Not shown is the manipulation of the fiber as listed in Table 1, which also occurs within the E3 module. Lastly, the E4 region was deleted and replaced with a single module. More specific information on the deletions and insertions can be found in the materials and methods. After altering these Adsembly vectors, they were used in standard Adsembly reactions to create viruses that contain one or more of the tumor diagnostic expression cassettes.

In one aspect, a method of detecting a cancer in a subject is provided. The method includes administering a recombinant reporter adenovirus to a subject. The recombinant reporter adenovirus is allowed to infect a cancer cell within the subject thereby forming a reporter infected cancer cell. A sample including the reporter infected cancer cell is obtained from the subject and the reporter infected cancer cell is detected thereby detecting a cancer in the subject. A recombinant reporter adenovirus as provided herein is a recombinant adenovirus including at least one (e.g. one) sequence that encodes for a reporter protein. Non limiting examples of recombinant reporter adenoviruses are shown in Table 2 and FIG. 9. The recombinant reporter adenoviruses provided herein including embodiments are formed according to the methods as described in published application PCT/US2011/048006, which is herein incorporated in its entirety and for all purposes. The reporter protein may be a fluorescent protein (e.g. green fluorescent protein, red fluorescent protein) or it may be a protein that can be fluorescently labeled thereby becoming readily detectable. Fluorescent labeling can be achieved by binding a fluorescently labeled antibody to the reporter protein. In some embodiments, the recombinant reporter adenovirus includes a Cytomegalovirus promoter operable linked to a nucleic acid encoding for a fluorescent protein. In some further embodiments, the fluorescent protein is a green fluorescent protein. In some embodiments, the recombinant reporter adenovirus includes a E2F promoter operable linked to a nucleic acid encoding for a fluorescent protein. In some further embodiments, the fluorescent protein is a red fluorescent protein. In some embodiments, the recombinant reporter adenovirus includes a SRE promoter operable linked to a nucleic acid encoding for a fluorescent protein. In some further embodiments, the fluorescent protein is a yellow fluorescent protein. In some embodiments, the recombinant reporter adenovirus includes a SMAD-responsive promoter operable linked to a nucleic acid encoding for a fluorescent protein. In some further embodiments, the fluorescent protein is a red fluorescent protein.

In another aspect, a method of detecting a cancer in a subject is provided. The method includes obtaining from a subject a sample including a cancer cell. A recombinant reporter adenovirus is contacted with the cancer cell. The recombinant reporter adenovirus is allowed to infect the cancer cell thereby forming a reporter infected cancer cell and the reporter infected cancer cell is detected thereby detecting a cancer in said subject. In some embodiments, the detecting according to the methods provided herein includes detecting a reporter gene phenotype. In some further embodiments, the reporter gene phenotype is a fluorescent reporter gene phenotype. Where a cell (e.g. cancer cell) is infected with a recombinant reporter adenovirus as provided herein, the cell is infected with an amount of recombinant reporter adenovirus sufficient to express a reporter phenotype.

In another aspect, a method of determining whether a test compound inhibits growth of a cancer cell from a cancer patient is provided. The method includes obtaining from a subject a sample including a cancer cell. A recombinant reporter adenovirus is contacted with the cancer cell. The recombinant reporter adenovirus is allowed to infect the cancer cell thereby forming a reporter infected cancer cell. The reporter infected cancer cell is allowed sufficient time to grow. A level of growth of the reporter infected cancer cell is determined and the level is compared to a control level, wherein a low level compared to the control level indicates the test compound inhibits growth of the cancer cell from the patient. A control level as provided herein is the level of growth of a cancer cell in the absence of the test compound.

In some embodiments, the cancer according to the methods provided herein is lung cancer, skin cancer or breast cancer. In other embodiments, the cancer cell according to the methods provided herein is a circulating cancer cell. In some embodiments, the cancer cell is a premalignant cell. In some embodiments, the sample according to the methods provided herein is a bodily fluid. In some further embodiments, the bodily fluid is blood. In other embodiments, the bodily fluid is serum or plasma. In other embodiments, the bodily fluid is urine, saliva, a pulmonary tissue, bronchoalveolar lavage sample, or exhaled breath condensate.

In another aspect, a method of isolating a reporter infected cancer cell within a sample from a subject is provided. The method includes separating the reporter infected cancer cell from a non-infected cell, wherein the separating is at least partially based on an expressed reporter gene phenotype of the reporter infected cancer cell. In some embodiments, the reporter gene phenotype is a level of fluorescent activity. In other embodiments, the reporter gene phenotype is a level of cell growth. In other embodiments, the reporter gene phenotype is a level of aberrant cell morphology. In some embodiments, the method further includes allowing the reporter infected cancer cell sufficient time to grow, thereby expressing the expressed reporter gene phenotype. In some embodiments, the non-infected cell is a non-cancer cell. In other embodiments, the sample is a blood sample.

In another aspect, a method of detecting a cancer in a subject is provided. The method includes administering a recombinant reporter adenovirus provided herein including embodiments thereof to a subject. The recombinant reporter adenovirus is allowed to infect a cancer cell within the subject thereby forming a reporter infected cancer cell. A sample is obtained from the subject including the reporter infected cancer cell and the reporter infected cancer cell is detected thereby detecting a cancer in the subject.

In another aspect, a method of detecting a cancer in a subject is provided. The method includes obtaining from a subject a sample including a cancer cell. A recombinant reporter adenovirus provided herein including embodiments thereof is contacted with the cancer cell. The recombinant reporter adenovirus is allowed to infect the cancer cell thereby forming a reporter infected cancer cell and the reporter infected cancer cell is detected thereby detecting a cancer in the subject. In some embodiments, the method further includes administering a cancer treatment to the subject.

A method of determining whether a test compound inhibits growth of a cancer cell from a cancer patient is provided. The method includes obtaining from a subject a sample including a cancer cell and contacting a recombinant reporter adenovirus provided herein including embodiments thereof with the cancer cell. The recombinant reporter adenovirus is allowed to infect the cancer cell thereby forming a reporter infected cancer cell. The reporter infected cancer cell is allowed sufficient time to grow and a level of growth of the reporter infected cancer cell is determined. The level is compared to a control level, wherein a low level compared to the control level indicates the test compound inhibits growth of the cancer cell from the patient.

III. Compositions

Provided herein, inter alia, is a recombinant reporter adenovirus useful for diagnosis and detection of cancer cells. In one aspect, a recombinant reporter adenovirus including a cancer cell reporter module and a cancer cell binding module is provided. A cancer cell reporter module as provided herein includes a reporter gene encoding a reporter protein. A reporter protein may be a fluorescent protein (e.g. green fluorescent protein, red fluorescent protein) or it may be a protein that can be fluorescently labeled thereby becoming readily detectable. Fluorescent labeling can be achieved by binding a fluorescently labeled antibody to the reporter protein. A cancer cell binding module as provided herein is a molecule capable of binding a molecule expressed by a cancer cell (e.g. cellular receptor). The cell binding molecule may be a small molecule or a protein. In some embodiments, the cancer cell reporter module includes a cancer responsive promoter operably linked to a reporter gene. A cancer responsive promoter as provided herein is a promoter having an activity in a cancer cell, wherein the activity is detectably different from the activity of the promoter in a non-cancer cell. In some embodiments, the activity is decreased as compared to the activity of the promoter in a non-cancer cell. In other embodiments, the activity is increased as compared to the activity of the promoter in a non-cancer cell. In some further embodiments, the reporter gene is a fluorescent reporter gene.

In some embodiments, the recombinant adenovirus further comprises an immune evasion module. An immune evasion module as provided herein is a protein or polypeptide, which if expressed by the recombinant reporter adenovirus prevents the recombinant reporter adenovirus from being detected by the immune system of the cancer patient.

In some embodiments, the cancer cell reporter module is a first cancer cell reporter module and the recombinant reporter adenovirus further includes a second cancer cell reporter module and a third cancer cell reporter module. In some embodiments, the first cancer cell reporter module is capable of expressing a first reporter gene phenotype, the second cancer cell reporter module is capable of expressing a second reporter gene phenotype, and the third cancer cell reporter module is capable of expressing a third reporter gene phenotype. In some further embodiments, the first reporter gene phenotype, the second reporter gene phenotype, and the third reporter gene phenotype are each detectably different. In some embodiments, the first reporter gene phenotype is indicative of a first cancer, the second reporter gene phenotype is indicative of a second cancer, and the third reporter gene phenotype is indicative of a third cancer. In some further embodiments, the first cancer, the second cancer and the third cancer are independently different. In some embodiments, the first reporter gene phenotype, the second reporter gene phenotype and the third reporter gene phenotype are indicative of a single cancer.

IV. Kits

In another aspect, a kit for detecting cancer is provided. The kit includes a recombinant reporter adenovirus provided herein including embodiments thereof. In some embodiments, the kit includes reagents for separating cells (e.g. potential cancer cells) from a tissue or cell sample from a subject, such as those described herein (e.g. magnetic beads or other affinity based separation materials, stock buffers etc.). Thus, the kit can include antibodies or other reagents capable of specifically binding to at least one cell-specific marker. The kit can also include tubes or other containers for holding the sample during the processing and detection. The kit further includes instructions to administer the recombinant reporter adenovirus to the patient under conditions suitable for infecting a cell and detecting a cell.

In another aspect, a kit for screening a cancer drug is provided. The kit includes a cancer inhibiting compound and a recombinant reporter adenovirus provided herein including embodiments thereof. In some embodiments, the kit includes reagents for administering the cancer inhibiting compound (e.g. stock buffers) and table-top detection devices for detecting the reporter gene phenotype.

In another aspect, a kit for isolating a cancer cell is provided. The kit includes a device for detecting an expressed reporter gene phenotype and a recombinant reporter adenovirus provided herein including embodiments thereof. In some embodiments, the kit includes reagents for separating (isolating) cancer cells from a tissue or cell sample from a subject, such as those described herein (e.g. magnetic beads or other affinity based separation materials, stock buffers etc.). Thus, the kit can include antibodies or other reagents capable of specifically binding to at least one cancer cell-specific marker. The kit can also include tubes or other containers for holding the sample during the processing and detection. The kit further includes instructions to administer the recombinant reporter adenovirus to the patient under conditions suitable for infecting a cancer cell and detecting a cancer cell.

V. Specific Embodiments

Applicants intend is to develop a standardized automated platform that provides point-of-care diagnostics to inform clinical decisions at a level of molecular sophistication and prognostic power that is not possible with any other detection system, biomarkers or correlative gene expression signatures. A non-invasive test, which detects, enumerates, characterizes and isolates viable CTCs from the blood have been developed. This alerts the clinician to either the presence or progression of cancer from a primary lesion and informs the clinical decision as to how aggressively a patient should be treated depending on the number nature of circulating tumor cells and the tumor pathways which are deregulated by genetic aberrations. Further it can be determined which of the key cancer pathways are deregulated based on robust transcriptional reporters and molecular hallmarks using a rapid economic automated platform operated by a technician. The CTCs can be isolated and captured and directly tested for their ability to respond to different potential treatment regimens and inform the clinician's decision as to which treatment option is most likely to achieve maximal efficacy.

Virus Vectors that Provide Quantitative and Qualitative Data Regarding Tumor Pathways Through Fluorescent Protein Readouts Over 100,000 mutations have now been identified in tumor genomes (Stratton M R, Campbell P J, Futreal P A, Nature. 2009; 458(7239):719-24.19360079) of which there are at least 350 genes that exhibit recurrent mutations (Futreal P A et al., Nat Rev Cancer., 2004; 4(3):177-83.14993899). Despite this new genetic knowledge, the diagnosis, prognosis and treatment of cancer patients still largely relies on subjective histopathology, surrogate biomarkers of transformation, variable surface markers or correlative gene expression signatures. With advances in DNA sequencing, it may soon be possible to sequence the genome of every cancer patient's tumor. However, even if this is possible, these data will not reveal epigenetic modifications and key interactions within the tumor microenvironment that determine a tumor's phenotype, or allow one to predict a priori how these factors interact to determine a patient's clinical outcome or the response of their tumors to different therapies.

Despite the complexity and genetic variability of cancers, all tumors share phenotypes that determine their malignant potential, the so-called 'hallmarks of cancer', which are the result of mutations in a relatively small number of key pathways (FIG. 1, (Hanahan D, Weinberg R A, Cell, 2000; 100(1):57-70.10647931)). In individual tumors the mutations that deregulate these pathways vary but converge downstream on key transcriptional elements and effectors. For example, tumor self-sufficiency for growth factor signaling can result from mutations in RTKs, RAS, PTEN, PI-3K, or RAF, while the RB tumor suppressor pathway can be inactivated by mutations in RB itself, loss of p16 (point mutations and epigenetic silencing) or overexpression of Cyclins (Du W, Searle J S, Curr Drug Targets, 2009; 10(7):581-9.19601762; Shea C J, Cel, 2004; 116(2):235-46.14744434; Rossi D J, Weissman I L, Cell, 2006; 125(2):229-31.16630811; Gazdar A F, Oncogene, 2009; 28 Suppl 1:S24-31.19680293; Yuan T L, Cantley L C, Oncogene., 2008; 27(41):5497-510.18794884). The acquisition of these mutations and their resultant phenotypic traits is not simultaneous but often occurs over a long period of time and through progressive stages. The deregulation of these key molecular activities can be functionally determined using diagnostic transcriptional reporter and cell-based assays. For example, mutations in Rb or p16 result in activation of E2F driven promoters (Du W, Searle J S, Curr Drug Targets, 2009; 10(7):581-9.19601762; Shen C J, Cel, 2004; 116(2):235-46.14744434). Similarly, the nuclear versus cytoplasmic localization of SMAD is an indicator of TGFβ pathway signaling and metastasis (Shi Y, Massague J., Cell, 2003; 113(6):685-700.12809600). These transcriptional and cell-based fluorescent localization read-outs are being used individually as reporters of tumor pathway activities in basic research and drug screening applications.

Figure 2:
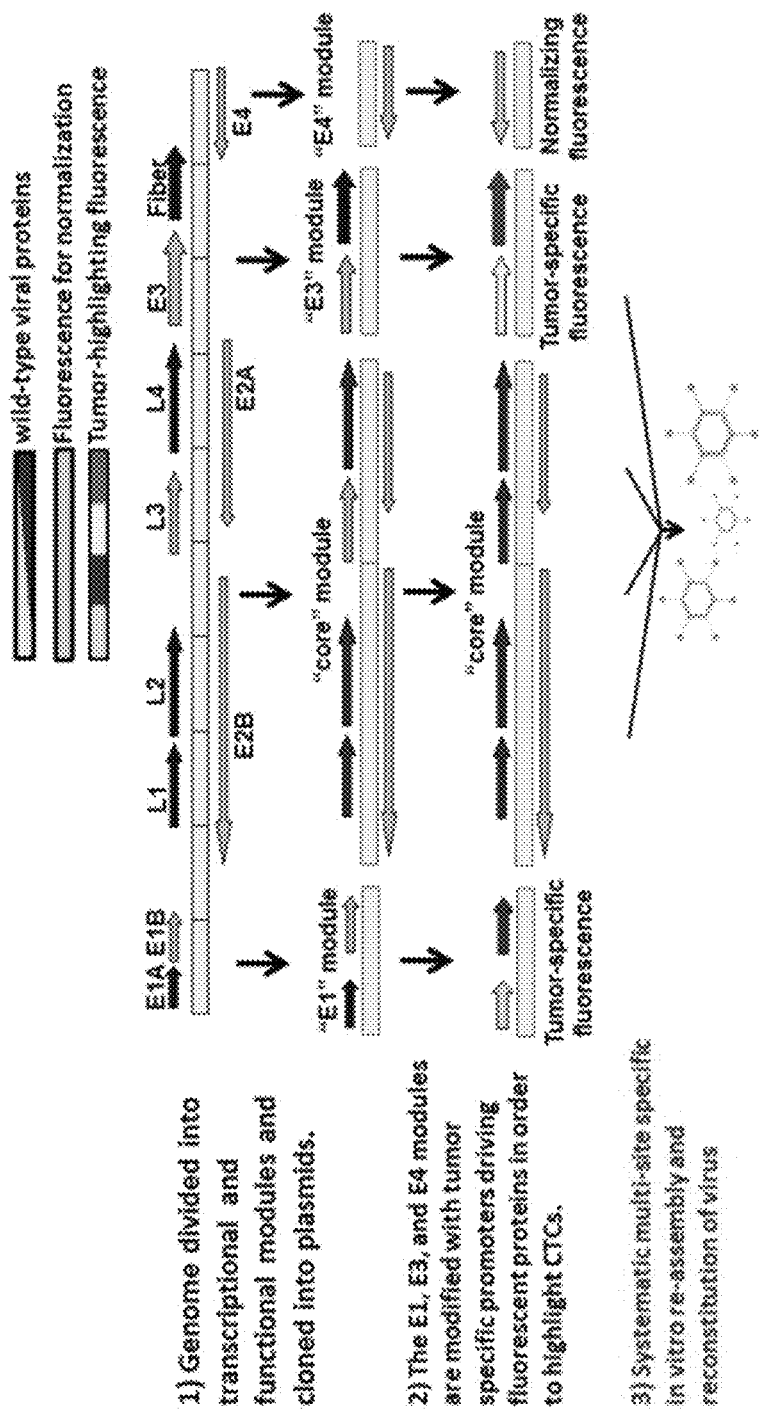
FIG. 2. Adsembly assembles Ad genomes from modular parts in rapid, in vitro reactions.

Rather than focusing on detecting individual genetic lesions that are numerous and highly variable between tumors, Applicants created viral diagnostic drones that incorporate multiple transcriptional and molecular modules in their genomes to detect a patient's tumor, report its molecular 'hallmarks' and 'up-front' response to different therapies. To achieve this Applicants exploit a transformative new technological platform that Applicants have recently developed to create next generation tumor selective replicating adenoviruses (O'Shea C C, Oncogene, 2005; 24(52):7636-9.16299525; O'Shea C C., Oncogene, 2005; 24(52):7640-55.16299526). Adenovirus is a natural multi-gene expression vehicle that reaches the nucleus within an hour of infection (O'Shea C C, Oncogene, 2005; 24(52):7636-9.16299525; O'Shea C C., Oncogene, 2005; 24(52):7640-55.16299526; Leopold P L, Crystal R G, Adv Drug Deliv Rev., 2007; 59(8):810-21.17707546). Applicants' 'Adsembly' enables the rapid, de novo assembly of custom adenoviral genomes in vitro from a library of genomic building parts (created from over 60 human and animal adenoviruses which have different tropisms and properties to Ad2/5 or which have been genetically modified to confer altered functionality) and heterologous elements (FIG. 2) (O'Shea C C, Oncogene, 2005; 24(52):7636-9.16299525). Applicants have already used this technology to create over 60 new viruses with various mutations and transgene expression cassettes, and have shown viruses created using this method are capable of high titer growth.

The E1, E3, and E4 regions are either not necessary for replication in culture or can be complemented with available cell lines (Goncalves M A, de Vries A A, Rev Med Virol., 2006; 16(3):167-86.16710837). Each of these regions has independent promoter elements that drive the expression of multiple gene products (16 genes) using alternative splicing. Applicants exploit this as a system to engineer single powerful diagnostic agents that incorporate multiplex and quantitative measurements of the pathway activities deregulated in different tumor samples (Table 1). The natural viral promoters are replaced with promoters that are activated in tumors with key mutations/phenotypes. These promoters drive the expression of four different fluorescent reporter gene-fusions which provide additional information on the key pathways deregulated in a patient's tumor, such as nuclear versus cytoplasmic NF-κB (inflammation), TORC2 (LKB1 mutations and metabolism), FOXO (PI3-K/AKT mutations) or SMAD 4 (TGFβ pathway mutations) (Shi Y, Massague J., Cell, 2003; 113(6):685-700.12809600; Oeckinghaus A, Ghosh S., Cold Spring Harb Perspect Biol., 2009; 1(4):a000034.20066092; Wullschleger S, Loewith R, Hall M N, Cell, 2006; 124(3):471-84.16469695; Weidinger C et al., Endocr Relat Cancer, 2008; 15(4):917-29.18775975). Using these agents, the molecular lesions and malignant characteristics of any given tumor can be rapidly discerned (within 24 hours) and scored via the NanoSort lab-on-a-chip μFACS. Furthermore, these agents could also be used as reporters to determine rapidly and directly if a patient's tumor is likely to respond to a particular therapy. Applicants' technology improves on previously described virus-based methods of CTC detection in several important ways (Fong S M et al., Surgery, 2009; 146(3):498-505.19715807; Kojima T et al., J Clin Invest., 2009; 119(10):3172-81.19729837). Through the use of Adsembly, libraries of tumor responsive fluorescent elements can be created. This allows for rapid creation of multiple adenoviruses tailored towards the detection of particular types of tumors and pathway mutations. Adsembly also allows for ease of retargeting adenovirus, thus maximizing chances of CTC transduction. Lastly, it allows for ease of multigene expression from the different genomic modules, which increases the amount of information that can be gained during CTC detection.

Lab-On-A-Chip Technology

Several methods have been proposed for improved CTC enumeration and capture and flow cytometry has already proven success (Allan A L, Keeney M., *J. Oncol.*, 2010; 2010:426218.20049168). Flow cytometry allows for rapid, yet highly specific, quantitative cell-by-cell analysis under multiple parameters, as well as the ability to sort CTCs for further molecular characterization. Additionally, flow cytometry is a mature, well-recognized, and commercially viable technology. However, multiple obstacles make current flow cytometers impractical for the point-of-care analysis of CTCs. First, cells must be labeled by manually pipetting individual antibodies into the cell samples. This procedure may result in large variations in data due to differences in antibody handling, pipetting inaccuracies, storage inconsistencies, and variability in antibody lots. Secondly, current flow cytometers are very expensive and have a large footprint (i.e. not mobile). Finally, current flow cytometers are technically and analytically challenging to operate.

To address these technical issues, Applicants have developed lab-on-a-chip technology that combines microfluidics, photonics, and microacoustics with groundbreaking analytical techniques. These patented technologies, exclusively licensed by NanoSort, Inc., enable point-of-care access to flow cytometry via a robust, portable, inexpensive device that meets or exceeds performance of current industry leaders at a fraction of the cost and space (Cho S H, Chen C H, Tsai F S, Godin J M, Lo Y H, *Lab Chip.*, 2010; 10(12):1567-73.20379604; Cho S H et al., *Conf Proc IEEE Eng Med Biol Soc.*, 2009; 2009:1075-8.19965141; Chen C H et al., *Biomed Microdevices*, 2009; 11(6):1223-31.19649710; Chen C H, et al., In: Hawkins A R, editor. Handbook of Optofluidics: CDC Press; 2010. p. 664; Godin J, Lo Y H, *Biomed Opt Express*, 2010; 1(5):1472-9.21258563).

Virus Based Detectors and Diagnostics Mediated Fluorescent Highlighting of Ctcs

Applicants created a series of tumor pathway activity modules that replace the viral E1, E3 and E4 transcriptional units, which have been re-assembled with additional modifications in the viral backbone to confer novel tissue tropisms and other activities. These viral diagnostic agents are validated in human tumor cell-lines (which have known phenotypes/mutations) as well as primary cells, and done so both in culture and in the context of human blood samples.

The first set of diagnostic adenoviruses has been engineered to express four different fluorescent biomarkers that are diagnostic of tumor cells with mutations in the RB/p16, TGFβ, Growth factor/PI-3K/Ras/MAPK, LKB1/AMPK pathways, not only labeling them for detection and collection, but defining their malignant potential and response to therapy. The latest data from the Sanger Center and Cosmic database shows that EGFR is amplified/mutated in 28% of tumors, RB (12%), p16 (13%), Ras (17%), LKB1 (9%), SMAD4 (2%). The feasibility of such an approach has already been demonstrated with the use of such tumor specific promoters for the development of oncolytic viruses to selectively induce the expression of viral genes in cancer, thereby ensuring tumor selective viral replication (O'Shea C C, *Oncogene*, 2005; 24(52):7636-9.16299525; O'Shea C C., *Oncogene*, 2005; 24(52):7640-55.16299526; Huang T G et al., *Gene Ther.*, 2003; 10(15):1241-7.12858189; McCormick F., *Cancer Biol Ther.*, 2003; 2(4 Suppl 1):S157-60.14508094; Ries S J, Brandts C H, *Drug Discov Today*, 2004; 9(17):759-68.15450242; Chiocca E A, *Nat Rev Cancer*, 2002; 2(12):938-50.12459732).

Figure 3:
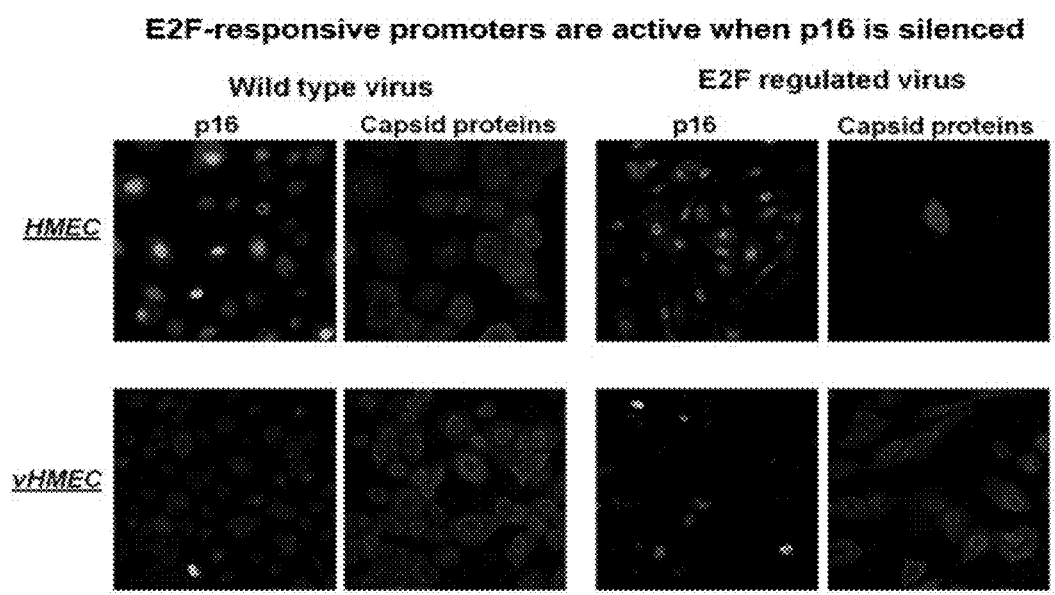
FIG. 3. E2F-responsive promoters are active when p16 is silenced.

For example, breast tissues from healthy women contain a subpopulation of variant human mammary epithelial cells (vHMEC) in which $p16^{INK4a}$ is epigenetically silenced (Hoist C R, *Cancer Res.*, 2003; 63(7):1596-601.12670910) and which are thought to represent premalignant precursors for breast cancer (Tlsty T D, *J Mammary Gland Biol Neoplasia*, 2004; 9(3):263-74.15557799; Crawford Y G et al., *Cancer Cell*, 2004; 5(3):263-73.15050918; Romanov S R et al., *Nature*, 2001; 409(6820):633-7.11214324). In FIG. 3, Applicants show that a virus in which the natural E1 promoter is replaced with the cellular E2F promoter (Johnson L et al., *Cancer Cell*, 2002; 1(4):325-37.12086848) specifically drives the expression of downstream viral proteins in vHMECs versus HMECs. Applicants use a similar strategy to detect and isolate CTCs but using replication incompetent viruses in which the viral genes are now replaced with fluorescent markers that enable their detection, quantification and sorting using an integrated lab-on-a-chip µFACS.

To achieve this, the viral "E1" module promoter and orfs are be replaced with an E2F promoter driving a TORC2-eYFP fusion. This identifies cells with mutations in the pRb/p16 pathway and LKB1. The viral "E3" module promoter and orfs are replaced with two cassettes. A CMV promoter regulated by a serum response element (SRE) drives mCherry, identifying hyperactivation of the EGFR/RAS/RAF/MAPK pathway and a TGFβ regulated promoter drives mOrange, identifying cells with metastatic potential. The viral "E4" module promoter and orfs are replaced with the CMV major IE promoter driving eGFP-FOXO, which are expressed in nearly all cells and serve both as a way to normalize fluorescence and identify cells with mutations in the PTEN/PI-3K/AKT pathways.

To ensure CTC infection, Applicants also incorporate a novel innovation. Ad5, which was first to be discovered, is the most predominant adenovirus used in basic and clinical research. The cellular receptor for Ad5 is CAR, which together with E-cadherin marks epithelial cells. However, CAR expression is often downregulated in cells undergoing an epithelial to mesenchymal transition (EMT), such as may occur in metastases. To infect and detect these cells Applicants have created and validated several fiber pseudotyped viruses that bind to different cellular receptors, such as CD46, thereby maximizing the chances of CTC transduction (Table 2).

This initial series of five viruses, each targeting an alternate receptor but all containing the same expression cassettes, are validated in primary lung and breast epithelial cells versus a panel of lung and breast cancer cell-lines with known molecular lesions (Neve R M et al., *Cancer Cell*, 2006; 10(6):515-27.17157791). Cells are transduced at an MOI=30 with each of the five viruses for 24 hours followed by fluorescent detection using FACS and microscopy. Upon confirmation of tumor selective gene expression in culture, Applicants optimize viral transduction in the context of human blood samples. It has previously been demonstrated that both replication competent (Kojima T et al., *J Clin Invest.*, 2009; 119(10):3172-81.19729837) and replication defective adenoviral vectors (Lyons M et al., *Mol Ther.*, 2006; 14(1):118-28.16580883) can transduce cells in whole blood samples, including samples spiked with tumor cells. 7.5 mL of expired whole blood obtained from the blood bank are treated with an erythrocyte lysis buffer containing ammonium chloride. The samples are then be spiked with lung or breast cancer cells at 1, 10, 100, or 1000 cells per mL of blood (Punnoose E A, et al., *PLoS ONE.* 2010; 5(9): e12517). Primary lung or breast epithelial cells are spiked as a negative control. Two transduction scenarios are examined. In one, cells are pelleted and the mix of five viruses are added to the samples at concentrations of $10^4$, $10^5$, and $10^6$ PFU of each virus. In the second, virus is added to whole blood without pelleting the cells. After addition of virus, the cells are incubated at 37° C. rocking for 16 or 24 h, collected by centrifugation, washed 2× with PBS, and sorted via µFACS.

NanoSort-UCSD Bench-Top µFACS for CTC Isolation

Figure 4:
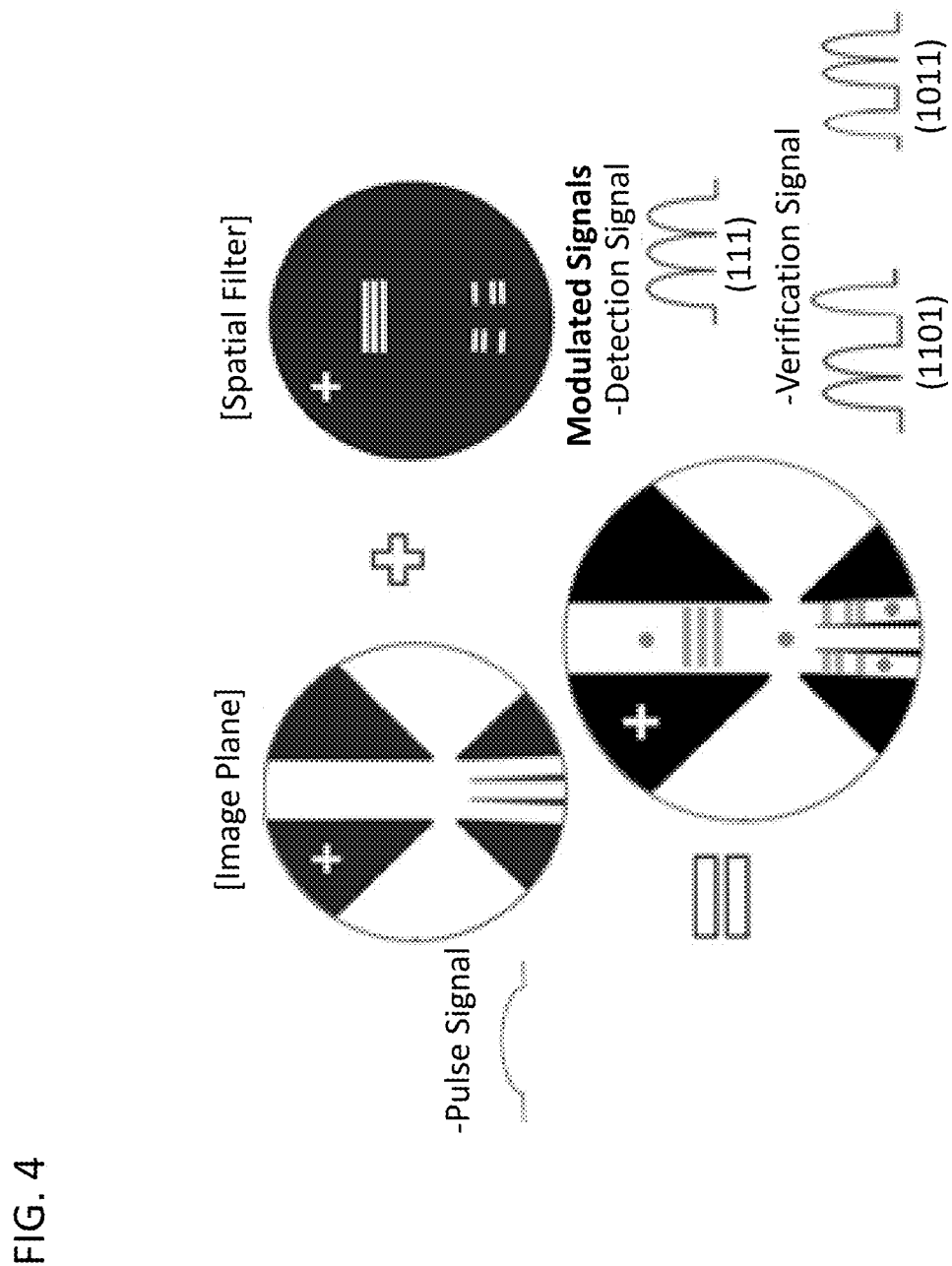
FIG. 4. Spatial filters (masks) are placed at the magnified image of the device feature. The input fluorescence pulse signal from stained cells is modulated by different spatial filters before being registered by the PMT, yielding different waveforms of photocurrents in time domain, corresponding to different locations of the cells as they travel through the microfluidics channel, such as (111), (1101) or (1011). This space-time coding technology reduces the size and the cost of the system by using only one PMT to differentiate 3 signals or even more.

NanoSort is developing the only fully functional lab-on-a-chip micro-fluorescence-activated-cell-sorter (µFACS) prototype using technology from Yuhwa Lo's UCSD laboratory that was partially supported by several NIH NCRR grants (Cho S H, Chen C H, Tsai F S, Godin J M, Lo Y H, *Lab Chip.*, 2010; 10(12):1567-73.20379604; Cho S H et al., *Conf Proc IEEE Eng Med Biol Soc.,* 2009; 2009:1075-8.19965141; Chen C H et al., *Biomed Microdevices,* 2009; 11(6):1223-31.19649710; Chen C H, et al., In: Hawkins A R, editor. Handbook of Optofluidics: CDC Press; 2010. p. 664). The lab-on-a-chip µFACS uses on-chip optical waveguides and a unique design of space-time coding architecture for fluorescence and scattering detection. Following the optical interrogation, the device uses an integrated piezoelectric disk actuator to sort single cells by displacing a finite volume (100 pL to 1 nL) of fluid. FIG. 4 shows a typical space-time coded fluorescent signal (1110) from a photomultiplier tube (PMT) detector at the detection spot, followed a short time later by another space-time coded signal (1011) to verify the successful sorting (Cho S H et al., *Conf Proc IEEE Eng Med Biol Soc.,* 2009; 2009:1075-8.19965141; Godin J, *J. Biophotonics.,* 2008; 1(5):355-76.19343660). This offers a unique feature to verify the success of individual sorting events and assure retention of every CTC. Should the detection signal (encoded as 1110) register but the subsequent (1011) signal not register, the system immediately detects that a CTC has escaped the sorter. In this event, the user may elect to process the sample a second time to capture the CTC.

Figure 5:
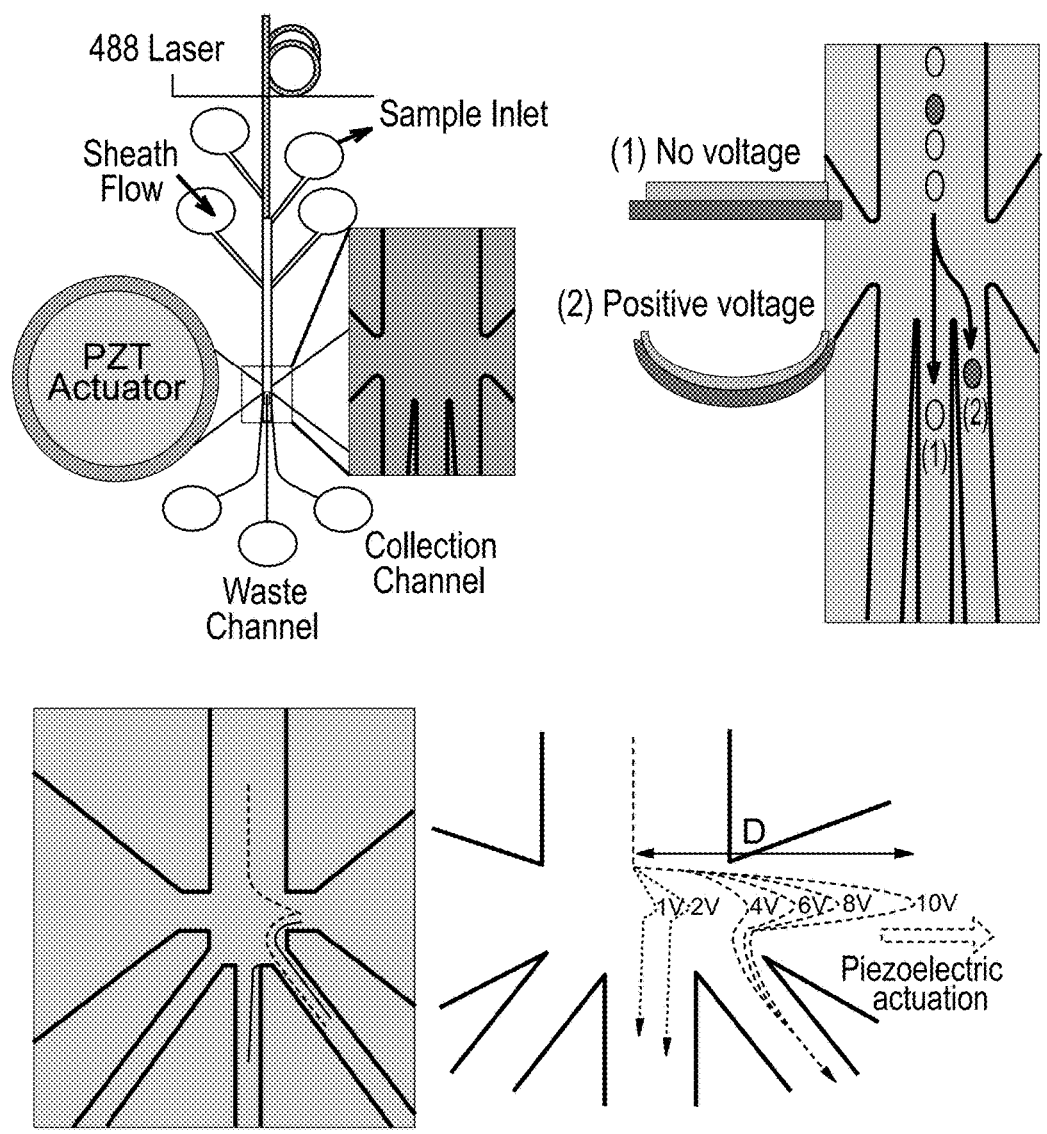
FIG. 5. Device structure (upper left). The 250 µm wide main fluidic channel is split into three sub-channels. The center channel is for collecting waste, while the left and the right channels are for collecting samples. The illumination light (488 nm laser) is delivered to the device by the optical fiber and guided by the Teflon AF coated optofluidic waveguide. The PZT actuator is integrated on the device. In the square is the sorting junction of the device made of PDMS. As the PZT actuator bends down, the cell of interest is pushed to the right sorting channel, while the non-targeted cell travels directly to the center waste channel without triggering the PZT (upper right). Flow pattern observation (bottom). Left: Trace of a fluorescent bead sorted to the right channel by superimposing photos taken every 0.3 ms using a high-speed CMOS camera. Right: The bead trajectory plot for the bead under different voltage magnitudes to the PZT actuator. This helps set the threshold voltage for sufficient deflection.
Figure 6:
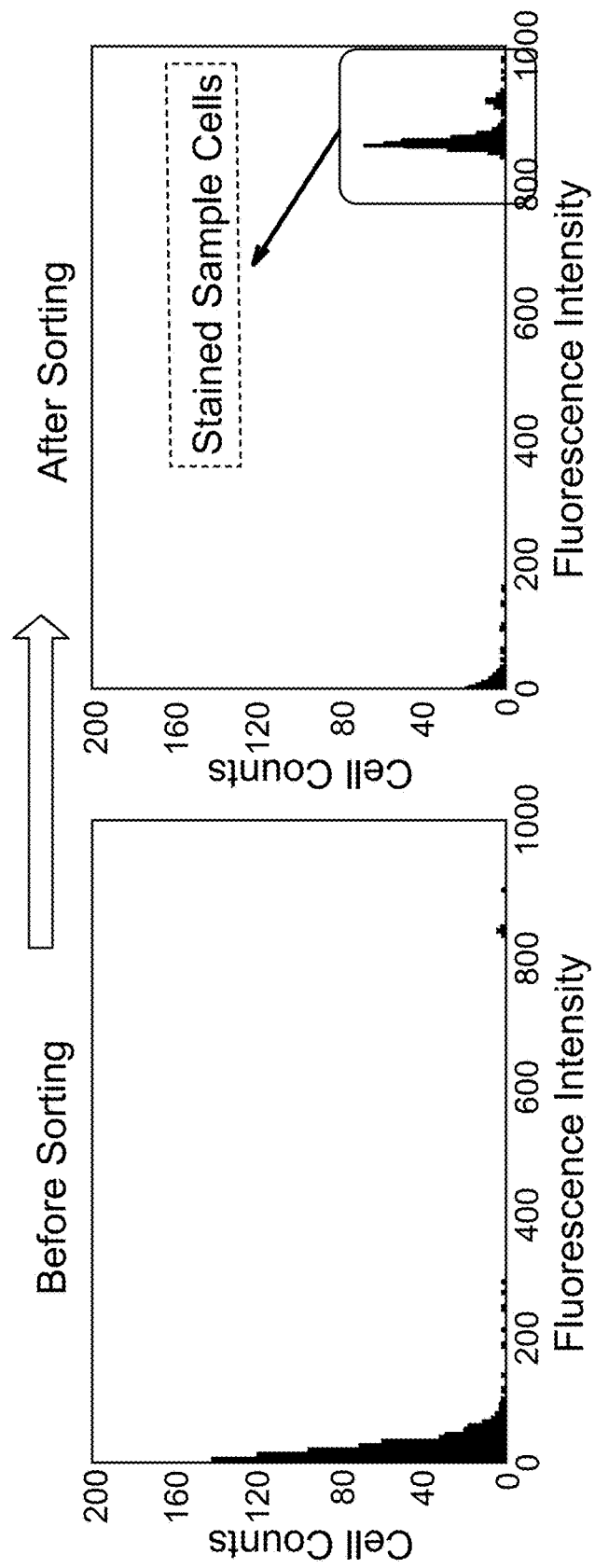
FIG. 6. Demonstration of sorting fluorescein stained erythroleukemic (K562) cells from unstained cells using the NanoSort-UCSD µFACS system. An enrichment factor of 230-fold was achieved (40).

FIG. 5 shows schematically the principle of the piezoelectric sorter and how effectively the on-chip sorter can switch the flow. The flow switching speed shown here is limited by the speed of Applicants' CCD camera, and the actual flow switching speed, thus the sorting speed, is several times faster in practice. FIG. 6 shows the result of cell sorting and Table 1 summarizes the comparisons between NanoSort-UCSD's µFACS and BD's Mo-Flow system. Using the µFACS system, Applicants complete both the enumeration and isolation the CTCs.

FACS (fluorescence activated cell sorting) is used as the basic model with modification and optimization of the lab-on-a-chip design for CTC enumeration and isolation. These modifications include the design of the piezoelectric sorter and the microfluidic flow confinement. Optimized sorting uses a design that maximizes the collection efficiency to assure each individual CTC is sorted, in contrast with the current design that optimizes speed over specificity. Regarding flow confinement, the current design uses sheath flow to produce lateral flow confinement and uses "chevron patterns" invented by Naval Research Laboratory to achieve flow confinement in the transverse direction (Howell P B, Jr., *Lab Chip,* 2008; 8(7):1097-103.18584084). However, the "chevron" design is less effective for large suspended cells (e.g. CTCs) because of the strong lift force (Godin J. *Optical Systems for Integration with Microfluidics.* La Jolla: University of California, San Diego; 2010). Applicants will investigate and optimize alternative flow confinement designs (e.g. utilizing the inertial forces and eccentric force in curved channels (Bhagat A et al., *Microfluidics and Nanofluidics,* 2009; 7(2):217-26; Bhagat A A S et al., *Physics of Fluids,* 2008; 20(10):101702-4; Di Carlo D et al., *Anal Chem,* 2008; 80(6):2204-11.18275222; Di Carlo D et al., *Proc Natl Acad Sci USA,* 2007; 104(48):18892-7.18025477) to improve CTC confinement and focusing in the flow stream. Improved CTC confinement in the flow stream reduces the coefficient of variation (CV) of the fluorescent and scattering signals, which can reduce the enumeration errors.

Figure 7:
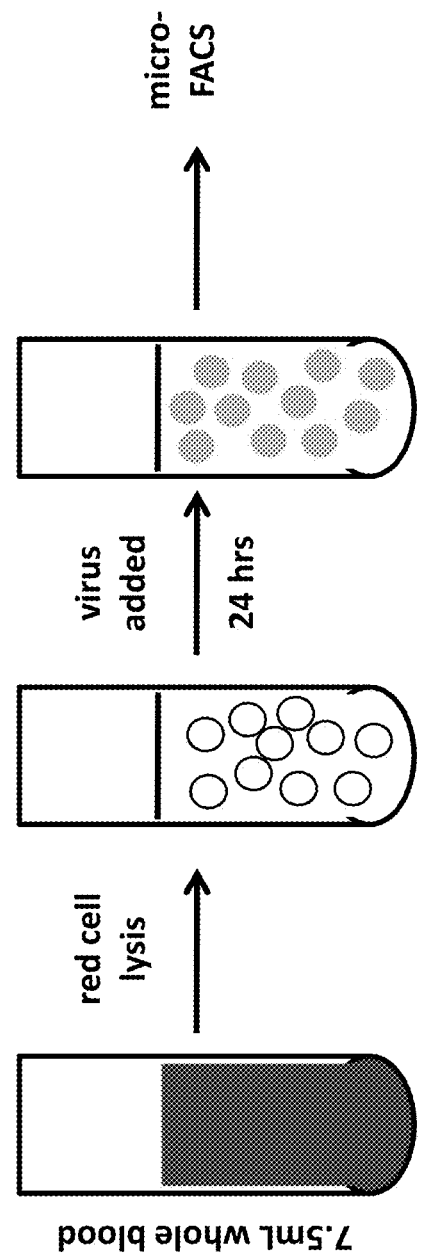
FIG. 7. Work flow and expected fluorescent readouts from transduced CTCs.
Figure 8:
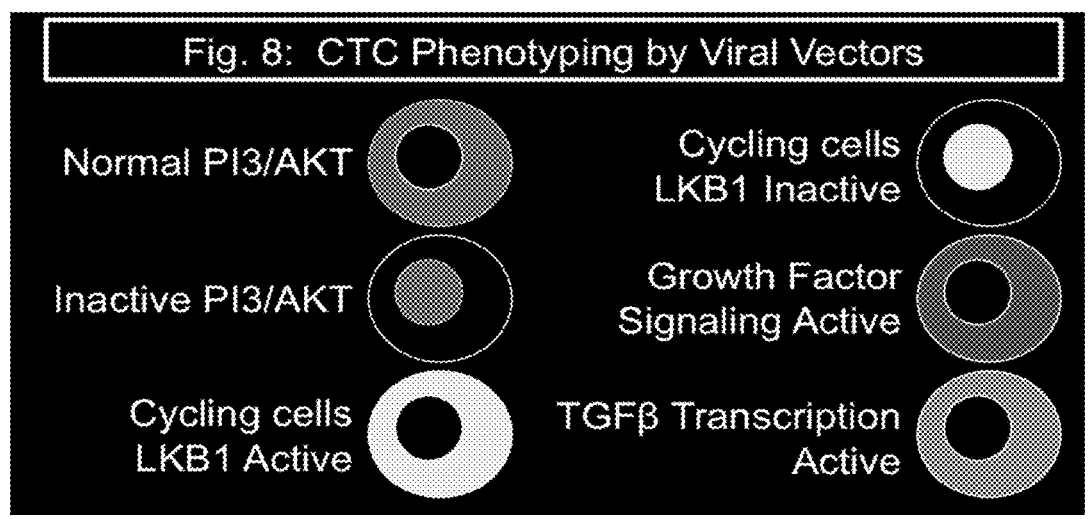
FIG. 8. CTC Phenotyping by Viral Vectors.

Samples are tested using the NanoSort device. Applicants then use commercial flow cytometers (e.g. FACSAria, BD) to measure the cell concentration in the "collected sample" and the "waste". The cell ratio between the collected sample and the waste produces the enumeration accuracy and sorting efficiency Combining Use of Tumor Selective Fluorescent Viral Vectors and µFACS to Detect and Isolate CTCs from Clinical Blood Samples In order to validate the use of both the tumor specific fluorescent viral vectors and the µFACS technologies in clinical samples, Applicants will obtain peripheral blood samples from Stage 1V non-small cell lung cancer patients from UCSD Moore's Cancer Center. This particular tumor is appropriate for Applicants' viruses as it is of epithelial origin (CD45−, EpCAM+ and cytokeratin 8 and 18+, and/or cytokeratin 19+) and can be validated using the CellSearch CTC platform (Veridex). Additionally, this tumor is particularly suitable for Applicants' viruses as it is a natural and primary target of several different human adenoviruses. 7.5 mL of whole blood will be collected in heparinized tubes and treated with erythrocyte lysis buffer containing ammonium chloride. The pool of five viruses will be then added to the sample and incubated at 37° C. with rocking for 24 hours. After transduction, cells will be pelleted at 1000×g, washed 2× with PBS, and sorted via µFACS. Cells that fluoresce over background will be collected for further processing by microscopy. Applicants will determine cytoplasmic or nuclear staining that will be diagnostic of hallmarks of cancer (FIGS. 7 and 8).

The NanoSort experimental protocol will be compared to the best commercially available system, CellSearch (Veridex) for validation. Both methods will analyze 7.5 mLs of blood. CellSearch will be carried out by a clinical laboratory (ApoCell, Houston, Tex.). Results will be analyzed and discussed by the team and prepared for publication in a peer-reviewed publication.

VI. Experimental Procedures

All vectors were manipulated from Ad5 Adsembly vectors.

Creation of the ΔE1 {SREp-YFP}-{CMVp-[Foxo3-GFP]} Plasmid

The backbone of the plasmid pENTR Ad5 ΔE1 CMV-GFP was obtained by PCR. This fragment contains a deletion of positions 376-3514 of the Ad5 genome (GenBank Accession AC_000008/GI:56160529F) with an insertion of the CMV promoter driving eGFP. The SRE promoter was obtained by PCR from plasmid pSRE-luc, and the BGH polyadenylation signal was obtained by PCR from the plasmid pCDNA3. The SRE promoter and BGH polyA were combined into the pENTR Ad5 ΔE1 CMV-GFP backbone using sequence and ligation independent cloning (SLIC) to create plasmid pENTR Ad5 ΔE1 SREp-CMV-GFP. This also generated a PacI restriction enzyme site between the SRE promoter and the BGH polyA signal. The Foxo3 cDNA was obtained by PCR from the plasmid containing its cDNA in the Ultimate ORF Collection (Invitrogen). It was fused by SLIC directly to the N-terminus of GFP in the backbone of plasmid pENTR Ad5 ΔE1 SREp-CMV-GFP, which was obtained by PCR. This generated the plasmid pENTR Ad5 ΔE1 SREp-CMV-[Foxo3-GFP]. Lastly, the cDNA for lanYFP was obtained by PCR from the plasmid pLanYFP-NT and cloned by SLIC into PacI-cut plasmid pENTR Ad5 ΔE1 SREp-CMV-[Foxo3-GFP]. This generated plasmid pENTR ΔE1 {SREp-YFP}-{CMVp-[Foxo3-GFP]}.

Creation of the Series of ΔE3 [SMADrp-tdTomato] Plasmids

The following series of changes were made to each of these five plasmids: pENTR Ad5 E3, pENTR Ad5 E3 Ad5/3 fiber, pENTR Ad5 E3 Ad5/11 fiber, pENTR Ad5 E3 Ad5/34 fiber, and pENTR Ad5 E3 Ad5-RGD fiber. First, the TATA box sequence in the E3 promoter at position 27539-27542 (GenBank Accession AC_000008) was mutated to CATC by site directed mutagenesis. Also, the ATF binding site at position 27509-27514 was mutated from TCGTCA to TAGGCA. These two changes reduce basal activity of the E3 promoter in order to reduce false positive readouts. The backbones of these vectors were then obtained by PCR to delete the E3A and E3B region (positions 28130-30807), and a SMAD-responsive promoter (SMADrp) followed by a PacI restriction site was inserted into this backbone using SLIC. Lastly, tdTomato was obtained by PCR and inserted into the PacI-digested vectors using SLIC.

Creation of the ΔE4 {E2F1p-[mCherry-CRTC2]} Plasmid

The plasmid backbone of pENTR Ad5 E4 was obtained by PCR to delete positions 32927-35815 of the Ad5 genome and combined with the E2F1 promoter followed by a PacI restriction site using SLIC. The E2F1 promoter was obtained by PCR from the DNA of the virus ONYX-411. This generated plasmid pENTR Ad5 ΔE4 E2F1p. The CRTC2 cDNA was obtained by PCR from the plasmid containing its cDNA in the Ultimate ORF Collection, and the mCherry cDNA was obtained from plasmid pmcherry-C1. CRTC2 was fused to the C-terminus of mCherry with an amino acid linker of SGLRS and cloned into the PacI-digested vector pENTR Ad5 ΔE4 E2F1p using SLIC. This created plasmid pENTR Ad5 ΔE4 {E2F1p-[mCherry-CRTC2]}.

Regarding PCRs, all PCRs were performed using the Phusion enzyme (NEB). All PCRs were performed with 1×HF buffer, 200 μM each dNTP, 0.5 μM each primer, and 10 ng of template. PCR conditions were as follows: 98° C. 30 sec-10 cycles of 98° C. 10 sec, 65° C. 30 sec(decrease temp 1° C. every 2 cycles), 72° C. for 30 sec for every 1 kb of PCR product length, 72° C. for 5 min, 4° C. hold.

Regarding SLIC, linear fragments are exonuclease treated for 12 min at room temp in the following 20 μl reaction: 50 mM Tris pH8, 10 mM MgC12, 50 μg/mL BSA, 200 mM Urea, 5 mM DTT, and 0.5 μl T4 DNA polymerase. The reaction is stopped by addition of 1 μl 0.5M EDTA, followed by incubation at 75° C. for 20 min. An equal amount of T4-treated DNAs are then mixed to around 20 μl in volume in a new tube. For SLIC combining 2 fragments, 10 μl of each reaction is used. For SLIC combining 3 fragments, 7 μl of each reaction is used. Fragments are annealed by heating to 65° C. for 10 min, followed by a slow cool down decreasing the temperature 0.5° C. every 5 seconds down to 25° C. After annealing, 5 μl of the reaction is transformed and clones are screened.

Regarding the creation of viruses from the altered entry vector plasmids, they were created using the Adsembly genome assembly method. 20 fmol of a dual DEST vector is combined with 50 fmol of the Ad5 E1 entry vector and 10 fmol each of the Ad5 E3 and E4 entry vectors. These vectors are combined with 2 μl of LR Clonase II (Invitrogen) in a final volume of 10 μl. The reaction is incubated at 25° C. overnight (12-16 hours). The reaction is stopped by the addition of 1 μl of proteinase K (Invitrogen) and incubation at 37° C. for 10 minutes. Five μl of the reaction is then transformed into high competency bacteria (>1e9 cfu/μg) that are sensitive to the ccdB gene product. Colonies are subsequently isolated and screened for complete genomes. A positive clone was transfected into 293-E4 cells using FuGENE6 (Roche) according to the manufacturer's instructions, and virus recovered after five days.

Transduction of primary and tumor cells to examine fluorescent readouts from viruses. Normal, non-tumor cells and various tumor cells are plated onto microscope chamber slides. The next day, the media is removed and virus inoculum added. Virus inoculum is at a total multiplicity of infection equal to 30. After 2 hours, the inoculum is removed and fresh medium added. After 24 hours, cells are washed 1× in PBS and fixed in 4% paraformaldehyde for 30 minutes. Following fixation, the cells are washed 1× in PBS and fluorescent imaging performed.

VII. Tables

TABLE 1

Quantitative and qualitative measurements of CTC

| Cancer Phenotype/ Hallmark | Tumor Pathways and Mutations | Virus Diagnostic Drone Element |
|---|---|---|
| Growth Factor independence | RTK & TK, RAS, RAF, PI-3K, PTEN, TSC1/2, LKB1 | FOXO nuclear export mTOR dependent UTRs TORC2 nuclear translocation |
| | Hormone signals (AR, ER, RXR) | Nuclear p42/p44 MAPK ER/AR promoters (eg PSA) SRE promoter |
| Insensitivity to anti-growth signals | Rb, p16, TGFβ, Cyclin D/CDK, MYC | E2F promoter Nuclear/Phospho SMAD |
| Resistance to apoptosis | P53, ARF, FAS/TNFR, BCL2 | p53 activated promoter |
| Sustained angiogenesis | VEGF, FGF, VHL | VEGF promoter HIF promoter and degradation |
| Tissue invasion and melastasis | E-padherin APC/β-catenin mutations Wnt TGFβ | Nuclear/Phospho SMAD Viral uptake TCF/LEF promoter Nuclear β-catenin |
| Inflammation | NF-κB Interferon | Nuclear NF-κB/Jun IRE promoters |

TABLE 2

Viruses created for cancer diagnostics
An initial panel of adenoviruses created for cancer diagnostics. An abbreviated virus name is listed in column 1.
The following four columns list each part of the cancer-diagnostic expression cassettes encoded by the viruses.
This includes the promoter used, the fluorescent protein readout for that promoter, the protein fused to the
fluorescent protein if applicable (Fluor fusion), and the polyadenylation signal used (polyA signal). The sixth
column indicates the serotype from which the fiber knob protein was obtained for that virus. Ad-RGD refers to an
Ad5 fiber that contains an RGD peptide motif inserted into the HI-loop of the fiber. The final column describes
what phenotype will activate the promoter and where the fluor fusion will be localized in the cell, if applicable.
While this list only contains viruses with one or two expression cassettes, the cassettes from any given virus
could be combined with other cassettes, allowing for four or more expression cassette from a single virus.

| | Expression cassette(s) | | | | | |
|---|---|---|---|---|---|---|
| Virus | Promoter | Fluorescent protein | Fluor fusion | polyA signal | Fiber knob | Promoter activity and readout |
| ΔE1 {SREp-YFP}-{CMVp-[Foxo3-GFP]} | Serum response element | lan-YFP | none | BGH | Ad5 | On in response to growth factor signaling and mitogens |
| | hCMV immediate early | eGFP | FOXO3 | SV40 | Ad5 | Constitutive. GFP is nuclear when Akt is inactive, cytoplasmic when Akt is active. |
| ΔE3 {SMADp-tdTomato} | SMAD-responsive | tdTomato | none | Ad5 E3 | Ad5 | On in response to TGF-β signaling. |
| ΔE3 {SMADp-tdTomato}; Ad5/3 fiber | SMAD-responsive | tdTomato | none | Ad5 E3 | Ad3 | On in response to TGF-β signaling. |
| ΔE3 {SMADp-tdTomato}; Ad5/11 fiber | SMAD-responsive | tdTomato | none | Ad5 E3 | Ad11 | On in response to TGF-β signaling. |
| ΔE3 {SMADp-tdTomato}; Ad5/34 fiber | SMAD-responsive | tdTomato | none | Ad5 E3 | Ad34 | On in response to TGF-β signaling. |
| ΔE3 {SMADp-tdTomato}; Ad5-RGD fiber | SMAD-responsive | tdTomato | none | Ad5 E3 | Ad5-RGD | On in response to TGF-β signaling. |
| ΔE4 {E2F1p-[mCherry-CRTC2]} | human E2F1 | mCherry | CRTC2 | Ad5 E4 | Ad5 | On when pRB is inactive. mCherry is nuclear when LKB1 is inactive, cytoplasmic when LKB1 is active. |

VIII. Embodiments

Embodiment 1

A method of detecting a cancer in a subject, said method comprising: (i) administering a recombinant reporter adenovirus to a subject; (ii) allowing said recombinant reporter adenovirus to infect a cancer cell within said subject thereby forming a reporter infected cancer cell; (iii) obtaining from said subject a sample comprising said reporter infected cancer cell; and (iv) detecting said reporter infected cancer cell thereby detecting a cancer in said subject.

Embodiment 2

A method of detecting a cancer in a subject, the method comprising: (i) obtaining from a subject a sample comprising a cancer cell; (ii) contacting a recombinant reporter adenovirus with said cancer cell; (iii) allowing said recombinant reporter adenovirus to infect said cancer cell thereby forming a reporter infected cancer cell; and (iv) detecting said reporter infected cancer cell thereby detecting a cancer in said subject.

Embodiment 3

A method of determining whether a test compound inhibits growth of a cancer cell from a cancer patient, said method comprising: (i) obtaining from a subject a sample comprising a cancer cell; (ii) contacting a recombinant reporter adenovirus with said cancer cell; (iii) allowing said recombinant reporter adenovirus to infect said cancer cell thereby forming a reporter infected cancer cell; (iv) allowing said reporter infected cancer cell sufficient time to grow; (v) determining a level of growth of said reporter infected cancer cell; and (vi) comparing said level to a control level, wherein a low level compared to said control level indicates said test compound inhibits growth of said cancer cell from said patient.

Embodiment 4

A method of one of embodiments 1, 2 or 3, wherein said cancer is lung cancer, skin cancer or breast cancer.

Embodiment 5

A method of one of embodiments 1, 2 or 3, wherein said cancer cell is a circulating cancer cell.

Embodiment 6

A method of one of embodiments 1, 2 or 3, wherein said cancer cell is a premalignant cell.

Embodiment 7

A method of one of embodiments 1, 2 or 3, wherein said sample is a bodily fluid or a tissue sample.

Embodiment 8

The method of embodiment 7, wherein said bodily fluid is blood.

Embodiment 9

The method of one of embodiments 1 or 2, wherein said detecting comprises detecting a reporter gene phenotype.

Embodiment 10

The method of embodiment 9, wherein said reporter gene phenotype is a fluorescent reporter gene phenotype.

Embodiment 11

A method of isolating a reporter infected cancer cell within a sample from a subject, said method comprising separating said reporter infected cancer cell from a non-infected cell, wherein said separating is at least partially based on an expressed reporter gene phenotype of said reporter infected cancer cell.

Embodiment 12

The method of embodiment 11, further comprising allowing said reporter infected cancer cell sufficient time to grow, thereby expressing said expressed reporter gene phenotype.

Embodiment 13

The method of embodiment 11, wherein said non-infected cell is a non-cancer cell.

Embodiment 14

The method of embodiment 11, wherein said sample is a blood sample.

Embodiment 15

A recombinant reporter adenovirus comprising, a cancer cell reporter module and a cancer cell binding module.

Embodiment 16

The recombinant reporter adenovirus of embodiment 15, further comprising an immune evasion module.

Embodiment 17

The recombinant reporter adenovirus of embodiment 15, wherein said cancer cell reporter module comprises a cancer responsive promoter operably linked to a reporter gene.

Embodiment 18

The recombinant reporter adenovirus of embodiment 17, wherein said reporter gene is a fluorescent reporter gene.

Embodiment 19

The recombinant reporter adenovirus of embodiment 15, wherein said cancer cell reporter module is a first cancer cell reporter module and said recombinant reporter adenovirus further comprises a second cancer cell reporter module and a third cancer cell reporter module.

Embodiment 20

The recombinant reporter adenovirus of embodiment 19, wherein said first cancer cell reporter module is capable of expressing a first reporter gene phenotype, said second cancer cell reporter module is capable of expressing a second reporter gene phenotype, and said third cancer cell reporter module is capable of expressing a third reporter gene phenotype.

Embodiment 21

The recombinant reporter adenovirus of embodiment 20, wherein said first reporter gene phenotype, said second reporter gene phenotype, and said third reporter gene phenotype are each detectably different.

Embodiment 22

The recombinant reporter adenovirus of embodiment 20, wherein said first reporter gene phenotype is indicative of a first cancer, said second reporter gene phenotype is indicative of a second cancer, and said third reporter gene phenotype is indicative of a third cancer.

Embodiment 23

The recombinant adenovirus of embodiment 22, wherein said first cancer, said second cancer and said third cancer are independently different.

Embodiment 24

The recombinant reporter adenovirus of embodiment 20, wherein said first reporter gene phenotype, said second reporter gene phenotype and said third reporter gene phenotype are indicative of a single cancer.

Embodiment 25

A method of detecting a cancer in a subject, said method comprising: (i) administering a recombinant reporter adenovirus of one of embodiments 15-24 to a subject; (ii) allowing said recombinant reporter adenovirus to infect a cancer cell within said subject thereby forming a reporter infected cancer cell; (iii) obtaining from said subject a sample comprising said reporter infected cancer cell; and (iv) detecting said reporter infected cancer cell thereby detecting a cancer in said subject.

Embodiment 26

A method of detecting a cancer in a subject, the method comprising: (i) obtaining from a subject a sample comprising a cancer cell; (ii) contacting a recombinant reporter adenovirus of one of embodiments 15-24 with said cancer cell; (iii) allowing said recombinant reporter adenovirus to infect said cancer cell thereby forming a reporter infected cancer cell; and (iv) detecting said reporter infected cancer cell thereby detecting a cancer in said subject.

Embodiment 27

The method of one of embodiments 25 or 26, further comprising administering a cancer treatment to said subject.

Embodiment 28

A method of determining whether a test compound inhibits growth of a cancer cell from a cancer patient, said method comprising: (i) obtaining from a subject a sample comprising a cancer cell; (ii) contacting a recombinant reporter adenovirus of one of embodiments 15-24 with said cancer cell; (iii) allowing said recombinant reporter adenovirus to infect said cancer cell thereby forming a reporter infected cancer cell; (iv) allowing said reporter infected cancer cell sufficient time to grow; (v) determining a level of growth of said reporter infected cancer cell; and (vi) comparing said level to a control level, wherein a low level compared to said control level indicates said test compound inhibits growth of said cancer cell from said patient.

Embodiment 29

A kit for detecting cancer, said kit comprising a recombinant reporter adenovirus of one of embodiments 15-24.

Embodiment 30

A kit for screening a cancer drug, said kit comprising a cancer inhibiting compound and a recombinant reporter adenovirus of one of embodiments 15-24.

Embodiment 31

A kit for isolating a cancer cell, said kit comprising a device for detecting an expressed reporter gene phenotype and a recombinant reporter adenovirus of one of embodiments 15-24.

The invention claimed is:

1. A recombinant reporter adenovirus, comprising a first cancer cell reporter module, a second cancer cell reporter module and a cancer cell binding module, wherein said first cancer cell reporter module comprises a constitutive promoter active in tumor cells and non-tumor cells operably linked to a first reporter gene that expresses a first reporter gene phenotype in tumor cells and non-tumor cells, and said second cancer cell reporter module comprises a cancer responsive promoter operably linked to a second reporter gene that expresses a second reporter gene phenotype in tumor cells, and wherein said first reporter gene phenotype and said second reporter gene phenotype are detectably different.

2. The recombinant reporter adenovirus of claim 1, further comprising an immune evasion module.

3. The recombinant reporter adenovirus of claim 1, wherein said first reporter gene or said second reporter gene comprises a fluorescent reporter gene.

4. The recombinant reporter adenovirus of claim 1, further comprising a third cancer cell reporter module, wherein said third cancer cell reporter module comprises a cancer responsive promoter operably linked to a third reporter gene that expresses a third reporter gene phenotype in tumor cells, wherein said first reporter gene phenotype, said second reporter gene phenotype, and said third reporter gene phenotype are each detectably different.

5. A method of detecting a cancer in a subject, said method comprising:
   (i) administering the recombinant reporter adenovirus of claim 1 to a subject;
   (ii) allowing said recombinant reporter adenovirus to infect a cancer cell within said subject thereby forming a reporter infected cancer cell;
   (iii) obtaining from said subject a sample comprising said reporter infected cancer cell; and
   (iv) detecting said reporter infected cancer cell thereby detecting a cancer in said subject.

6. The method of claim 5, wherein said detecting comprises detecting a reporter gene phenotype.

7. A method of detecting a cancer in a subject, the method comprising:
   (i) obtaining from a subject a sample comprising a cancer cell;
   (ii) contacting the recombinant reporter adenovirus of claim 1 with said cancer cell;
   (iii) allowing said recombinant reporter adenovirus to infect said cancer cell thereby forming a reporter infected cancer cell; and
   (iv) detecting said reporter infected cancer cell thereby detecting a cancer in said subject.

8. The method of claim 7, wherein said detecting comprises detecting a reporter gene phenotype.

9. A method of determining whether a test compound inhibits growth of a cancer cell from a cancer patient, said method comprising:
   (i) obtaining from a subject a sample comprising a cancer cell;
   (ii) contacting the recombinant reporter adenovirus of claim 1 with said cancer cell;
   (iii) allowing said recombinant reporter adenovirus to infect said cancer cell thereby forming a reporter infected cancer cell;
   (iv) allowing said reporter infected cancer cell sufficient time to grow;
   (v) determining a level of growth of said reporter infected cancer cell; and
   (vi) comparing said level to a control level, wherein a low level compared to said control level indicates said test compound inhibits growth of said cancer cell from said patient.

10. A kit for detecting cancer, for screening a cancer drug and/or for isolating a cancer cell, said kit comprising the recombinant reporter adenovirus of claim 1 and (i) reagents for separating cells from a tissue or cell sample from a subject; (ii) a cancer inhibiting compound; and/or (iii) a device for detecting an expressed reporter gene phenotype.

11. The recombinant reporter adenovirus of claim 1, wherein the cancer cell binding module comprises an adenovirus fiber protein that binds CD46.

12. The recombinant reporter adenovirus of claim 1, wherein the cancer cell binding module comprises an Ad3, Ad11 or Ad34 fiber knob.

13. The recombinant reporter adenovirus of claim 1, wherein the cancer responsive promoter is active only in:
    (a) pRb/p16 inactive cells;
    (b) cells with an activated EGFR/RAS/RAF/MAPK pathway; or
    (c) cells with active transforming growth factor (TGF)-β signaling.

14. The recombinant reporter adenovirus of claim 13, wherein the cancer responsive promoter is E2F, serum response element (SRE) or a SMAD-responsive promoter.

15. The recombinant reporter adenovirus of claim 1, wherein the first reporter gene and/or the second reporter gene encodes a fusion protein comprising a fluorescent protein and a protein that directs localization of the fusion protein to either the cytoplasm or the nucleus.

16. The recombinant reporter adenovirus of claim 15, wherein the protein that directs location of the fusion protein comprises FOXO3 or CRTC2.

17. The recombinant reporter adenovirus of claim 1, wherein the first reporter gene or the second reporter gene encodes a green fluorescent protein, a yellow fluorescent protein or a red fluorescent protein.

18. The recombinant reporter adenovirus of claim 17, wherein the fluorescent protein comprises mCherry or tdTomato.

* * * * *